United States Patent [19]
Cohenford et al.

[11] Patent Number: 6,031,232
[45] Date of Patent: Feb. 29, 2000

[54] METHOD FOR THE DETECTION OF MALIGNANT AND PREMALIGNANT STAGES OF CERVICAL CANCER

[75] Inventors: Menashi A. Cohenford, West Warwick, R.I.; Prashant S. Bhandare, Arlington, Mass.; Frederick R. Cahn, Princeton, N.J.; Krishnaswamy Krishnan, Norwell, Mass.; Basil Rigas, White Plains, N.Y.

[73] Assignee: Bio-Rad Laboratories, Inc., Hercules, Calif.

[21] Appl. No.: 08/558,130

[22] Filed: Nov. 13, 1995

[51] Int. Cl.$^7$ ..................................................... G01N 21/35
[52] U.S. Cl. ................ 250/339.09; 128/664; 250/339.12
[58] Field of Search ..................................... 128/664, 665; 250/339.01, 339.06, 341.1, 339.12, 339.09

[56] References Cited

U.S. PATENT DOCUMENTS

| | | |
|---|---|---|
| 4,975,581 | 12/1990 | Robinson et al. . |
| 4,980,551 | 12/1990 | Wong . |
| 5,036,853 | 8/1991 | Jeffcoat et al. ........................... 128/634 |
| 5,038,039 | 8/1991 | Wong et al. . |
| 5,168,162 | 12/1992 | Oong et al. .............................. 250/339 |
| 5,197,470 | 3/1993 | Helfer et al. ............................. 128/634 |
| 5,435,309 | 7/1995 | Thomas et al. .......................... 128/633 |
| 5,539,207 | 7/1996 | Wong ................................. 250/339.08 |
| 5,596,992 | 1/1997 | Haaland et al. ......................... 128/664 |

OTHER PUBLICATIONS

Rigas, et al., *Proc. Natl. Acad. Sci. USA*, 87:8140–8145 (1991).
Rigas, et al., *Cancer Research*, 52:84–88 (1992).
Morris, et al., *Gynecologic Oncology* 56:245–249 (1995).
Haaland, et al., *Anal. Chem.* 60:1193–1202 (1988).
Cahn, et al., *Applied Spectroscopy*, 42:865–872 (1988).
Ge, et al., *Applied Spectroscopy* 49:432–436 (1995).
Wong et al., *Proc. Natl. Acad. Sci. USA*, 88:10988–10992 (1991).
Geladi, et al., *Analytica Chimica Acta*, 185:1–17 (1986).
Kozoni, et al., *Oncological Archives*, see Summary, 4:20 (1995).
Wong, et al., *Applied Spectroscopy*, 44(10):1715–1718 (1990).
Wong, et al., *Applied Spectroscopy*, 45(9):1563–1567 (1991).
Wong, et al., *Applied Spectroscopy*, 47(7):1058–1063 (1993).

*Primary Examiner*—Ruth S. Smith
*Attorney, Agent, or Firm*—Townsend and Townsend and Crew LLP

[57] ABSTRACT

This invention discloses a method to identify premalignant and malignant stages of cervical cancer from an infrared (IR) spectrum of exfoliated cervical cells which are dried on an infrared transparent matrix and scanned at the frequency range from 3000–950 cm$^{-1}$. The identification of samples is based on establishing a calibration using a representative set of spectra of normal, dysplastic and malignant specimens. During the calibration process, multivariate techniques such as Principal Component Analysis (PCA) and/or Partial Least Squares (PLS) are used. PCA and PLS reduce the data based on maximum variations between the spectra, and generate clusters in a multidimensional space representing the different populations. The utilization of Mahalinobis distances, or linear regression (e.g., Principle Component Regression on the reduced data from PCA) form the basis for the discrimination. This method is simple to use and achieves statistically reliable distinction between the following groups of cervical smears: normal (individuals with no prior history of dysplasia), dysplasia and malignant samples. Lastly, this invention discloses a method to obtain the IR spectrum of individual cervical cells fixed on an infrared transparent matrix.

12 Claims, 6 Drawing Sheets

METHOD FOR THE DETECTION OF MALIGNANT AND PREMALIGNANT STAGES OF CERVICAL CANCER

BACKGROUND OF THE INVENTION

The detection of premalignant and malignant cells by the Papanicolaou smear (Pap smear) has greatly reduced the high mortality rate due to cervical cancer. Nevertheless, the Pap screening process is labor intensive and has remained essentially unchanged since it was first described by Papanicolaou almost 50 years ago. To perform the test, exfoliated cells from a patient's cervix are first scraped using a spatula or brush. The scraping is then smeared on a slide, and the slide is stained and microscopically examined. The microscopic examination is a tedious process, and requires a cytotechnologist to visually scrutinize all the fields within a slide to detect the often few aberrant cells in a specimen. Consequently, the rate in the detection of abnormal specimens depends on the level of a cytotechnologist's experience, quality of the smear preparation, and the work load. As a result of these concerns, attempts have been made both to automate the Pap screening process, and develop other objective alternatives.

A number of methods have been explored to detect cytological anomalies, including those using molecular and immunological techniques. One impetus behind the development of new molecular and immunological methods is the detection of the human papilloma virus (HPV). Certain subtypes of HPV have been linked to a high incidence of abnormal lesions, and are implicated in the etiology of cervical cancer. Although these techniques are specific and detect cervical specimens at high risk, they are currently cost prohibitive and too labor intensive.

Recently, differences have been reported in the Fourier Transform Infrared (FT-IR) spectra of 156 cervical samples, of which, by cytological screening, 136 were normal, 12 had cancer, and 8 had dysplasia (see, Wong et al., *Proc. Natl. Acad. Sci. USA*, 87:8140–8145 (1991)). This study relied on features of the Mid-IR region (3000–950 $cm^{-1}$) to discriminate between the samples. The spectra of normal samples exhibited a prominent peak at 1025 $cm^{-1}$ which appears to be due to glycogen, and other less pronounced bands at 1047 $cm^{-1}$, 1082 $cm^{-1}$, 1155 $cm^{-1}$ and 1244 $cm^{-1}$. The spectra of specimens diagnosed with cancer exhibited significant changes in the intensity of the bands at 1025 $cm^{-1}$ and 1047 $cm^{-1}$, and demonstrated a peak at 970 $cm^{-1}$ which was absent in normal specimens. Samples with cancer also showed a significant shift in the normally appearing peaks at 1082 $cm^{-1}$, 1155 $cm^{-1}$ and 1244 $cm^{-1}$. The cervical specimens diagnosed cytologically as dysplasia exhibited spectra intermediate in appearance between normal and malignant. Based on these observations, Wong et al. concluded that FT-IR spectroscopy may provide a reliable and cost effective alternative for screening cervical specimens.

More recently, others have reported a greater diversity in the spectra of specimens with dysplasia than previously reported by Wong et al. (see Morris, et al., *Gynecologic Oncology* 56:245–249 (1995)). Out of the 25 specimens that were evaluated, the spectra of 9/13 specimens with low grade dysplasia (CIN I) appeared essentially similar to the spectra of normal specimens. However, as dysplasia progressed from low to high (CIN I to CIN III), the magnitude of spectral differences between normal and dysplastic samples intensified. This difference was most apparent in specimens with high grade dysplasia (CIN III) which exhibited a characteristic peak at 972 $cm^{-1}$, and changes in intensity of bands at 1026 $cm^{-1}$ (decreased), 1081 $cm^{-1}$ (increased and shifted to higher frequency), 1156 $cm^{-1}$ (decreased and flattened), and 1240 $cm^{-1}$ (increased).

The FT-IR spectroscopic studies of Wong, et al. (1991) focused primarily on the differences between normal and malignant samples, and utilized only a few dysplastic specimens. More importantly, discrimination between specimens was achieved by inspection of spectra, and by overt changes in peak intensity ratios at specified frequencies. Visual inspection as a basis of discrimination is not an ideal method of analysis. This approach lends itself to subjective bias and is frequently insensitive to small variations between spectra. In the case of malignant specimens, the spectral patterns are markedly altered compared to those of normal samples. However, as indicated earlier, the spectra of a great majority of specimens with low grade dysplasia (e.g. CIN I—cervical intraepithelial neoplasia) appear similar to spectra from normal samples and are difficult to distinguish. As a result, this method is unreliable and unsuited for the analysis of cervical specimens.

The method of selecting peak intensity ratios to discriminate between spectra has its problems too. This technique identifies general shapes and patterns, and like the previous approach lacks acuity in the detection of subtle differences between spectra. Other disadvantages of this method include its inability to model for interferences that may be caused by nondiagnostic debris, and/or errors that may result from sample preparation and handling techniques. Aside from the latter, this method also fails to adequately model for baseline shifts, spectral fringes, batch to batch variations in samples and/or to account for the nonlinearities that may arise from spectroscopic instrumentation and refractive dispersion of light.

Robinson, et al. in U.S. Pat. No. 4,975,581 issued Dec. 4, 1990 describe a quantitative method to determine the similarities of a biological analyte in known biological fluids using multivariate analysis. Although reliable, the method focuses on the in vivo evaluation of analytes in fluids, and uses noninvasive techniques. No accommodations are made to discriminate between solid biological material such as mammalian cells or to address the issues that may arise while discriminating the IR spectra of solid biological materials with varied path lengths outside the body.

From a clinical point of view, it is desirable to detect all specimens with dysplasia. The progression of dysplastic cells to cancer is not only well documented, but is also of fundamental importance in the Pap screening process. The present invention provides methods of detecting both malignant and premalignant stages of cervical cancer.

SUMMARY OF THE INVENTION

The present invention provides methods for the identification of a malignant or premalignant condition in an exfoliated cervical cell sample. The methods involve, (a) drying an exfoliated cervical cell sample on an infrared transparent matrix to produce a dried cell sample;

(b) directing a beam of mid-infrared light at the dried cell sample, the beam of mid-infrared light having a frequency of from about 3000 to about 950 $cm^{-1}$ to produce absorption data for the dried cell sample;

(c) comparing the absorption data for the dried cell sample with a calibration/reference set of infrared absorption data to determine whether variation in infrared absorption occurs in the dried cell sample, at at least one range of frequencies, due to the variation being characteristic of a malignant or premalignant condition.

The method of comparison utilizes a partial least squares or principal component analysis statistical method and is based on absorption data which is underivatized and unsmoothed. In particularly preferred embodiments, the calibration/reference set of infrared absorption data is obtained from a representative set of normal, dysplastic and malignant cervical cells which were dried on an infrared transparent matrix.

DETAILED DESCRIPTION OF THE INVENTION

Abbreviations and Definitions

Figure 1:
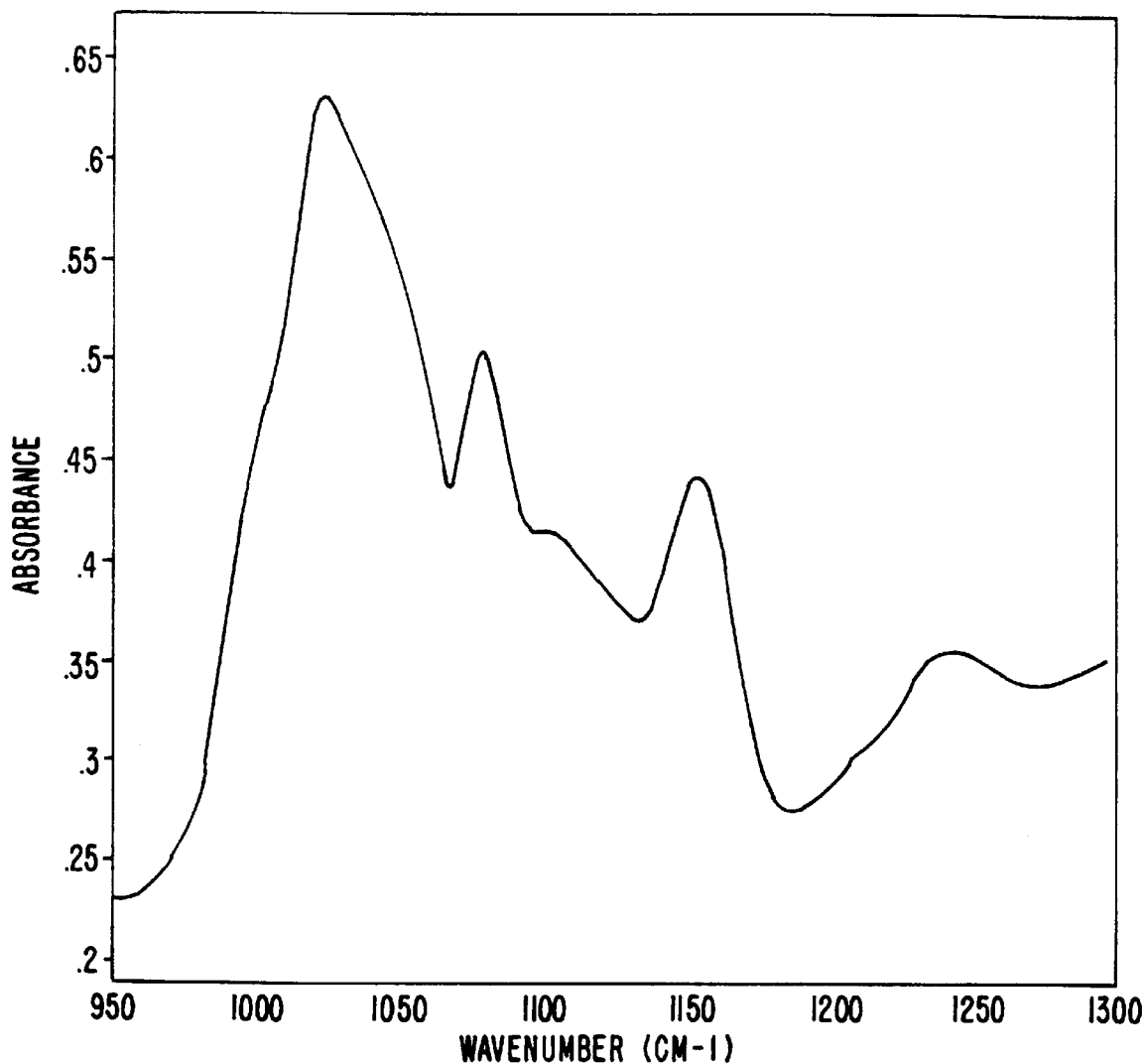
FIG. 1 shows the mid-infrared spectrum (from 950 $cm^{-1}$–1300 $cm^{-1}$) of a normal cervical scraping.

Abbreviations used herein have the following meanings: PCA, principal component analysis; PCR, principal component regression; PLS, partial least squares analysis.

As used herein, the terms "underivatized" and "unsmoothed" are used to refer to a process whereby no arithmetic manipulations have been applied to 1) enhance the slope or changes in the slope of spectra, and 2) reduce the random noise in spectra, respectively.

Description of the Embodiments

Discrimination between spectra of cervical specimens that have subtle variations requires the use of robust and sensitive methods of analysis. These methods must model for the nonlinearities that may arise due to various causes as well as account for the day to day drifts in instrument settings. Sample handling errors, spectral fringes, baseline shifts, batch to batch variations, the presence of nondiagnostic debris and all other factors that adversely affect discrimination must be also accounted adequately and modeled for. Water absorbs strongly in mid-infrared region and contributes to changes in intensity at several frequencies. Thus, the method of analysis must also consider the varying amounts of moisture in cervical specimens. Lastly, for a method to prove robust it must distinguish between good and poor quality spectra, and exclude or model for outlier samples. An outlier sample is a sample that is statistically different from all other samples in the calibration set. In the case of cervical scrapings, an outlier spectrum may result from samples with less than an optimal number of cells, and/or specimens that are rich in blood, mucus and/or nondiagnostic debris.

In one aspect, the present invention provides a method for the identification of a malignant or premalignant condition in an exfoliated cervical cell sample. This method comprises:

(a) drying the exfoliated cervical cell sample on an infrared transparent matrix to produce a dried cell sample;

(b) directing a beam of mid-infrared light at the dried cell sample, the beam of mid-infrared light having a frequency of from about 3000 $cm^{-1}$ to about 950 $cm^{-1}$ to produce absorption data for the dried cell sample; and (c) comparing the infrared absorption data for the dried cell sample with a calibration/reference set of infrared absorption data to determine whether variation in infrared absorption occurs in the dried cell sample, at least one range of frequencies, due to the variation being characteristic of the malignant or premalignant condition. The method of comparing utilizes a partial least squares (PLS) or principal component analysis (PCA) statistical method. Additionally, the absorption data is underivatized and unsmoothed.

In this method, the calibration/reference set of infrared absorption data is obtained from cell samples which have previously been identified as normal, dysplastic or malignant samples. Identification of these cell types is typically made by cytological examination such as the one performed on smears. The infrared absorption spectra for each of the identified cell types is obtained for the mid-infrared region from about 3000 $cm^{-1}$ to about 950 $cm^{-1}$. Typically, the calibration/reference set of infrared absorption data is prepared from about 100 to about 1000 reference cell samples, preferably from about 100 to about 500 reference cell samples.

In general, the calibration set should be representative of all expected variations in the spectra. The infrared absorption data of all samples is then processed with a computer utilizing PCA or PLS algorithms to extract information relating to each of the variations within the calibration spectra. The resulting information is used, thereafter, to distinguish between different groups of cervical specimens (e.g. normal, dysplastic or malignant).

The exfoliated cervical cell sample is collected by standard methods such as those used in collecting samples for Pap screening and applied to an infrared transparent matrix. A variety of matrices are available for use in the present invention. Preferred matrices are $BaF_2$, ZnS, polyethylene film, CsI, KCl, KBr, $CaF_2$, NaCl and ZnSe. A particularly preferred matrix is ZnS. Once the sample is applied to the matrix, the sample is dried to remove moisture which interferes with the infrared spectra. The methods used for drying will typically involve air-drying at ambient temperatures. Alternatively, the sample can be dried with controlled gentle heating, and by passing a stream of air or inert gas over the sample. For example, matrices with applied samples can be placed at 30° C. to 35° C. (e.g., a hot plate with temperature control knob to about 30–35° C.) and an atmosphere of, for example, air, nitrogen or argon can be passed over the samples to expedite their drying.

Others have relied on the utilization of a sample holder described in U.S. Pat. No. 4,980,551. Briefly, that device is made to accommodate a set of IR transparent windows in face to face contact, and contains the means to secure the windows in the path of an infrared light beam transmitting passage. The exterior of at least one of the windows has a surface portion contoured to provide between the windows a space for the sample. This sample space being shaped to provide adjacent light beam paths of different length minimizes optical interference fringes, and enhances the quality of spectra. To utilize the holder, contents from cervical scraping are first deposited in the sample space of one of the windows. With the other window carefully positioned over the specimen, the holder is tightened to secure the windows. An infrared light beam is passed through the sample space and the absorption of the cervical sample is recorded. Acquisition of spectra of cervical specimens by this technique is a difficult and time consuming process. For example, it is not only required that special windows be made, but also the biological specimen must remain undisturbed while being compressed between two windows. Compression frequently causes the leakage of tissue fluids, and ultimately the spilling of cervical specimens beyond the confines of the windows. Moreover, because cervical specimens may be contaminated with infectious agents such as the AIDS, Herpes and/or the various Hepatitis viruses, any leakage creates serious biological safety concerns. Still further, tissue fluids also absorb strongly in the mid-infrared region and contribute to changes in intensity at several frequencies.

In contrast, the methods of the present invention result in samples that are easy to manipulate and which provide high quality spectra. More importantly, drying eliminates the problems associated with tissue fluids, and reduces the risk of contamination by infectious agents. In a study of more than 100 cervical scrapings processed by this method, the direct deposition and drying of specimens was found to provide spectra with minimal or no fringes.

Another complication to the screening of cervical samples by infrared spectroscopy is the fact that only a few aberrant cells are generally recovered from the cervical scrapings of patients with dysplasia and cancer. For these cells to be detected by FT-IR spectroscopy, they must be present in the path of the infrared beam before analysis. One approach to ensure that the IR transparent windows contain a representative population of cells is to disperse the cervical scrapings prior to their deposit on the IR transparent windows. A thorough dispersion of the cervical scraping causes the separation of cells from surrounding nondiagnostic debris and mucus, provides a relatively uniform suspension of cells for spectral acquisition, and enhances the possibility of detecting the abnormal cells.

Thus, in some embodiments, the samples will be dispersed prior to their application to the infrared matrix. Dispersion of the cell sample is preferably carried out in a preservative solution which maintains the integrity of the exfoliated cells. The selection criteria for a preservative solution also necessitate that the preservative solution evaporates readily, and upon evaporation, leaves no residues that create interference in the infrared spectra of cervical scrapings. An example of one such preservative solution is PRESERV CYT® (CYTYC Corporation, Marlborough, Mass., U.S.A.). Following dispersion of the cell sample, the mixture is filtered to remove the nondiagnostic debris and the solution of cells is applied in a uniform layer to an infrared matrix, as described above, and dried.

Once the sample has been prepared (and dried) on the infrared matrix, a beam of mid-infrared light is directed at the sample and the absorption of the sample is monitored using any of a number of commercially available infrared spectrophotometers. Preferably, the spectrometer is a Bio-Rad Digilab FTS 165 spectrometer equipped with a DTGS detector. Other suitable spectrometers are known to those of skill in the art. Spectra are collected at a resolution of from about 2 $cm^{-1}$ to about 10 $cm^{-1}$, preferably from about 4 $cm^{-1}$ to about 8 $cm^{-1}$. Additionally, a number of scans are taken and co-added. Preferably about 50–500 scans are co-added, more preferably about 100–300 scans are co-added. In preferred embodiments, the spectra are normalized by setting the minimum absorbance at 0.0 and the maximum absorbance at 1.0 in the frequency regions between 3000 $cm^{-1}$ to 1000 $cm^{-1}$.

After collection of the infrared absorption data for the dried cell sample, the data is compared to the calibration/reference set to determine if variations exist in the sample which are characteristic of a malignant or premalignant condition. This comparison is typically carried out by a partial least squares (PLS) or principal component analysis (PCA) statistical method on absorption data for the sample which is preferentially unsmoothed and underivatized. Preferably, comparisons using principle component regression (PCR) are carried out using PCA. A number of computer programs are available which carry out these statistical methods, including PCR-32® (from Bio-Rad, Cambridge, Mass., U.S.A.) and PLS-PLUS® and DISCRIMINATE® (from Galactic Industries, Salem, N.H., U.S.A. ). Discussions of the underlying theory and calculations can be found in, for example, Haaland, et al., *Anal. Chem.* 60:1193–1202 (1988); Cahn, et al., *Applied Spectroscopy,* 42:865–872 (1988); and Martens, et al., MULTIVARIATE CALIBRATION, John Wiley and Sons, New York, N.Y. (1989).

Principal Component Analysis (PCA) and discriminate analysis has recently been employed to distinguish between normal and abnormal cervical scrapings. See, Zhengfang, et al., *Applied Spectroscopy* 49:432–436 (1995). However, the methods described therein did not focus on the detection of premalignant stages of cervical cancer and also relied on preprocessing algorithms that smoothed the spectra. Smoothing of spectra can obscure the subtle differences which exist between spectral patterns, and consequently can affect the discriminate analysis.

Although PCR and PLS have been used in various fields of science and in many types of applications, these techniques have never been used to discriminate in the mid-infrared region of the spectra, cervical scrapings from normal patients and patients with dysplasia or cervical cancer. Both PCR and PLS can reduce massive amounts of data into sets that can be readily managed for analysis. More importantly, when these methods are used to evaluate the spectra of mammalian cells, the techniques analyze entire regions of a spectrum and allow discrimination between the spectra of different groups of specimens.

Both PCR and PLS use a library of spectra from known materials with known concentrations to create a reference (calibration set). These spectra are acquired under the same experimental conditions. These techniques consist of spectral data compression (in the case of PCR, this step is known as PCA), and linear regression. Using a linear combination of factors or principal components, a reconstructed spectrum is derived. This reconstructed spectrum is compared with the spectra of unknown specimens which serves as the basis for classification.

Prior to the analysis of unknown samples, another set of spectra of the same materials are typically used to validate and optimize the calibration. This second set of spectra enhance the prediction accuracy of the PCR or PLS model by determining the rank of the model. The optimal rank is determined from a range of ranks by comparing the PCR or PLS predictions with known diagnoses. Increasing or decreasing the rank from what was determined optimal may adversely affect the PLS or PCR predictions. For example, as the rank is gradually decreased from optimal to suboptimal, PCR or PLS would account for less and less variations in the calibration spectra. In contrast, a gradual increase in the rank beyond what was determined optimal would cause the PCR or PLS methodologies to model random variation rather than significant information in the calibration spectra.

Generally, the more spectra a reference set includes, the better is the model, and the better are the chances to account for batch to batch variations, baseline shifts and the nonlinearities that may arise due to instrument drifts and changes in the refractive index. Errors due to poor sample handling and preparation, sample impurities, and operator mistakes can also be accounted for so long as the reference data render a true representation of the unknown samples.

Another major advantage to using PCR and PLS analysis is that these methods measure the spectral noise level of unknown samples relative to the calibration spectra. Biological samples are subject to numerous sources of perturbations. Some of these perturbations drastically affect the quality of spectra, and adversely influence the results of a "diagnosis". Consequently, it is imperative to distinguish between spectra that conform with the calibration spectra, and those that do not (e.g. the outlier samples). The F-ratio is a powerful tool in detecting conformity or a lack of fit of a spectrum (sample) to the calibration spectra. In general F-ratios considerably greater than those of the calibration indicate "lack of fit" and should be excluded from the analysis. The ability to exclude outlier samples adds to the robustness and reliability of PCR and PLS as it avoids the creation of a "diagnosis" from inferior and corrupted spectra. F-ratios can be calculated by the methods described in Haaland, et al., *Anal. Chem.* 60:1193–1202 (1988), and Cahn, et al., *Applied Spectroscopy* 42:865–872 (1988).

When discriminating between samples of different cervical scrapings, the biological materials no longer have known concentrations of constituents, and/or a constant path length. As a result, the calibration spectra must determine the range of variation allowed for a sample to be classified as a member of that calibration, and should also include preprocessing algorithms to account for diversities in path length. One normalization approach that aids in the discrimination of cervical specimens is locating the maximum and minimum points in a spectral region, and rescaling the spectrum so that the minimum remains at 0.0, and the maximum at 1.0 absorbance (e.g. in the frequency region between 3000 $cm^{-1}$ to 1000 $cm^{-1}$). Another normalization procedure is to select a specific peak(s) at a certain frequency(ies) of the IR spectra, and relate all other peaks to the selected peak(s). A third type of normalization is to normalize the magnitude of the absorbance vector before processing.

In preferred embodiments, comparison of the infrared absorption data for the sample and the data for the calibration/reference set utilizes principal component analysis in the frequency region 1200 $cm^{-1}$ to 1000 $cm^{-1}$, more preferably in the frequency regions of about 1250 to 1000 $cm^{-1}$, about 1420 to 1330 $cm^{-1}$ and about 3000 to 2800 $cm^{-1}$.

The Pap screening process renders a diagnosis based on the microscopic examination of each of the cells in a cervical scraping. Nevertheless, present spectroscopic techniques have used a bulk analysis of cervical scrapings. The use of Fourier Transform IR (FT-IR) spectroscopy, while capable of examining objects with sizes approaching 10 $\mu$m, is complicated by the presence of blood, mucus, and nondiagnostic debris in cervical scrapings. These materials may not only contribute to the clumping of the cells, but also create interferences that mask the actual spectra of cells in general. Nevertheless, it remains important to conclusively identify those cells that contribute to the changes in the spectra between normal and abnormal specimens. Thus, in one group of embodiments, the present method is carried out using a beam of mid-infrared light which is directed through an aperture of individual cell size, thereby providing absorption data for single cells. In this group of embodiments, the sample is dispersed and filtered, as described above, to create a uniform suspension of cells which can be applied to an infrared matrix and dried.

In another aspect, the present invention provides a method for the in vivo identification of a malignant or premalignant cervical condition in a host, comprising;

(a) directing a beam of infrared light through an optic fiber at the cervical cells in the host, at a range of frequencies to produce absorption data for the host;

(b) performing the analysis in mid or near infrared regions; and (c) comparing the absorption data for the cervical cells with a calibration/reference set of infrared absorption data to determine whether variation in infrared absorption occurs in the cervical cells, at at least one range of frequencies, due to the variation being characteristic of a malignant or premalignant condition, the comparing utilizing a partial least squares or principal component analysis statistical method and the absorption data being underivatized and unsmoothed, whereby an identification of a malignant or premalignant condition is made.

In preferred embodiments, the calibration/reference set of infrared absorption data from cervical cells is obtained from a representative population of normal, dysplastic and malignant hosts.

In the mid infrared region, use of the frequencies between 3000 $cm^{-1}$ to 950 $cm^{-1}$ is preferred. In the near IR, use of the frequencies between 12,500 $cm^{-1}$ to 4000 $cm^{-1}$ is preferred.

The techniques used in this aspect of the invention are generally the same as those described above. Differences are in the fundamental approach of in vivo collection of data and in the use of an optic fiber to direct the beam of mid or near infrared light. Typical optic fibers used for mid-Infrared include Chalcogenide, and Silver Halide. A typical optic fiber for near IR is the Quartz fiber. One advantage to in vivo analysis of cervical cells is that the method directs the physician to the site of anomalous tissue, and also minimizes the size of specimens for biopsy. Moreover, this method can provide a rapid objective screening of patients, while patients are being examined in a doctor's office. The current procedures necessitate that a physician sends Pap smears to a laboratory, where they are stained and evaluated by a cytotechnologist. Other benefits to the in vivo technique include the on-site treatment of suspicious tissues after localization by infrared spectroscopy.

In yet another aspect, the present invention provides a method for identifying a patient who is at high risk for dysplasia. In this method, a reference set of cervical cell samples is created from women having no history of dysplasia, each of the samples having a balance of two cell types. A mean and standard distribution for the balances from the reference samples is established and a cervical cell sample population from the patient is compared with the mean and standard distribution to determine if the balance of cell types from the patient is outside the mean and standard distribution from the reference set. In this manner, one can determine if the patient is at high risk for dysplasia.

In preferred embodiments, the two cell types are mature squamous cells and intermediate squamous epithelial cells. In other preferred embodiments, the balance of cells in the reference set and in the patient sample are identified by spectroscopic means (e.g., flow cytometry, infrared, ultraviolet, nuclear magnetic resonance). In other embodiments, the balance is determined visually with the aid of a microscope.

The following examples are offered solely for the purposes of illustration, and are intended neither to limit nor to define the invention.

EXAMPLES

Example 1

This example illustrates the detection of malignant and premalignant cervical cancer conditions using infrared spectroscopy with principal component analysis.

1.1 Materials and Methods

Four hundred thirty-six spectra were obtained from cervical scrapings collected by the method described in Wong, et al., *Proc. Natl. Acad. Sci. USA*, 88:10988–10992 (1991). The spectra and Pap smear diagnosis were analyzed for the feasibility of predicting Pap smear diagnosis by principle component analysis of the infrared spectra. Unless otherwise indicated, analysis was confined to the frequency region of 1200 cm$^{-1}$ to 1000 cm$^{-1}$. All spectra were normalized in the frequency region of 1200 cm$^{-1}$ to 1000 cm$^{-1}$ so that the minimum absorbance was set at 0.0 absorbance and the maximum at 1.0 absorbance.

1.2 Results

Figure 2:
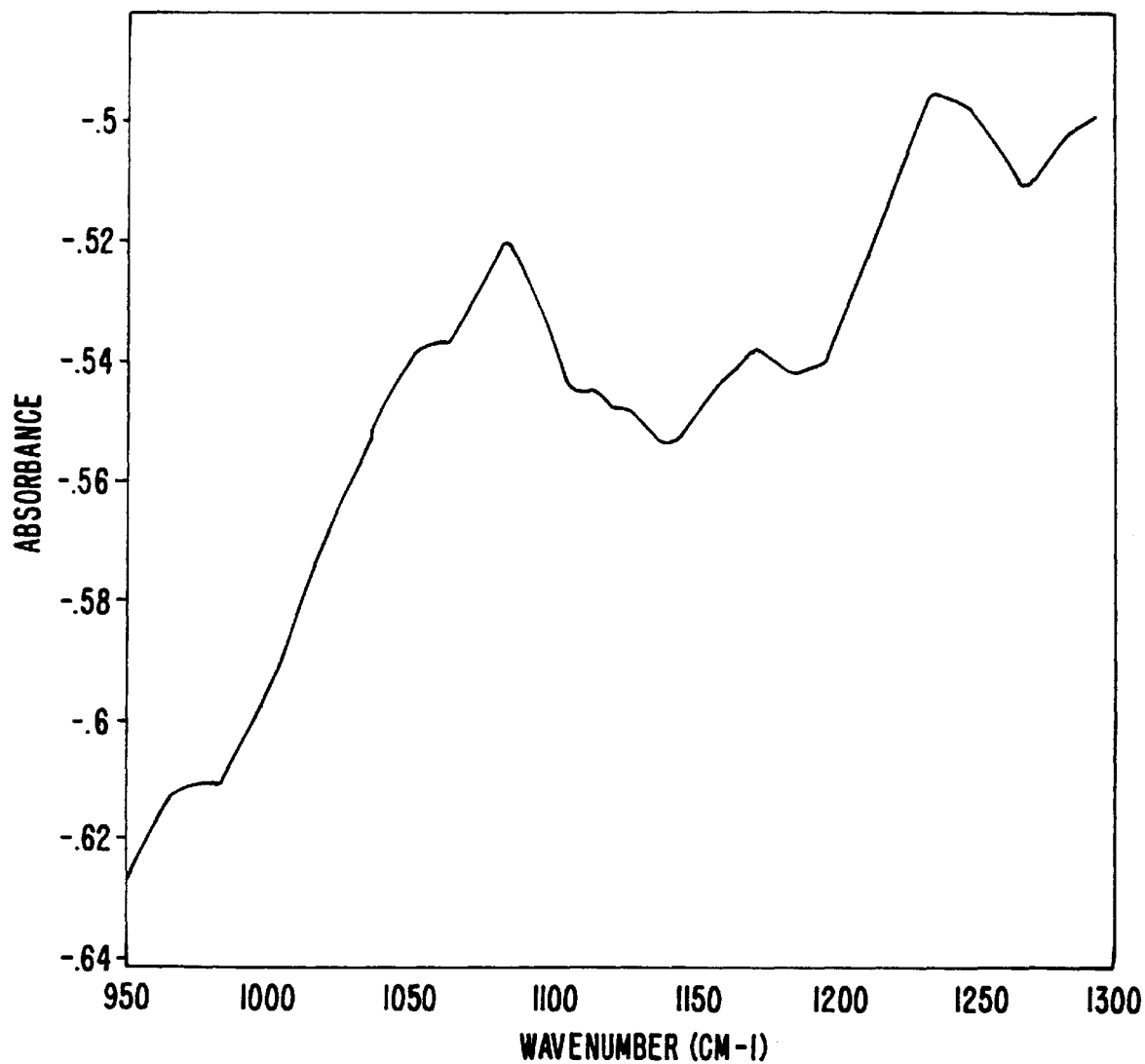
FIG. 2 shows the mid-infrared spectrum (from 950 $cm^{-1}$–1300 $cm^{-1}$) of a malignant cervical scraping.

Inspection of the spectra after normalization revealed two basic patterns. One pattern exhibited a prominent peak around 1025 cm$^{-1}$ (see FIG. 1), and had spectral features typical of those observed with normal cervical scrapings (see Wong, et al., ibid.). The second basic pattern manifested no peaks at or around the 1025 cm$^{-1}$ region (FIG. 2), and appeared 'typical' of the spectra which were reported for malignant specimens (Wong, et al., ibid.). In some cases, spectra appeared to be a mixture of the two patterns, and/or appeared atypical, or showed fringing. The initial analysis focused on samples that exhibited the 'typical' normal and malignant spectra, and excluded all other specimens with anomalous spectral features (e.g. with a mixed, or an atypical or fringed pattern).

A calibration set was then created on a subset of these preselected spectra as follows: one reference included the normal specimens with spectra 'typical' of normal cervical scrapings (FIG. 1), and the other of malignant samples with spectra typical of cancer. Spectra from normal cervical scrapings were assigned a dummy variable value of 0, and those from malignant scrapings were assigned a value of 1. Every 4th spectrum of the remaining subset of selected spectra was then used as a validation sample.

Table 1 summarizes the Sum of Squares (SS) of the spectra after mean centering as elucidated by each principal component. Calculation of these values was carried out by the methods described in Haaland, et al., *Anal. Chem.* 60:1193–1202 (1988), and in Cahn, et al., *Applied Spectroscopy* 42:865–872 (1988). Tabulated results show that over 99% of the variation in the spectra are accountable by the first 7 principal components.

TABLE 1

| PCA ANALYSIS OF CALIBRATION DATA SET | | |
|---|---|---|
| Rank | SS | Cumulative SS |
| 1 | 70.03% | 70.03% |
| 2 | 15.07% | 85.11% |
| 3 | 7.76% | 92.86% |

TABLE 1-continued

| PCA ANALYSIS OF CALIBRATION DATA SET | | |
|---|---|---|
| Rank | SS | Cumulative SS |
| 4 | 3.77% | 96.63% |
| 5 | 1.50% | 98.13% |
| 6 | 0.72% | 98.85% |
| 7 | 0.40% | 99.25% |
| 8 | 0.24% | 99.49% |
| 9 | 0.18% | 99.68% |
| 10 | 0.12% | 99.80% |

A rank of 7 was selected as providing the best discrimination on a cross validation analysis of the few randomly selected validation samples that were omitted from the calibration. This rank was selected on the basis of tabulating the minimum prediction of the malignant samples and the maximum prediction for the normal samples vs. PCR model rank (Table 2).

TABLE 2

| PREDICTED DUMMY VARIABLES VS. PCR MODEL RANK | | |
|---|---|---|
| Rank | Minimum malignant prediction | Maximum normal prediction |
| 1 | 0.93 | 0.14 |
| 2 | 0.95 | 0.10 |
| 3 | 0.92 | 0.16 |
| 4 | 0.92 | 0.19 |
| 5 | 0.90 | 0.09 |
| 6 | 0.94 | 0.09 |
| 7 | 0.95 | 0.08 |
| 8 | 0.95 | 0.08 |
| 9 | 0.95 | 0.12 |
| 10 | 0.94 | 0.11 |

Figure 3:
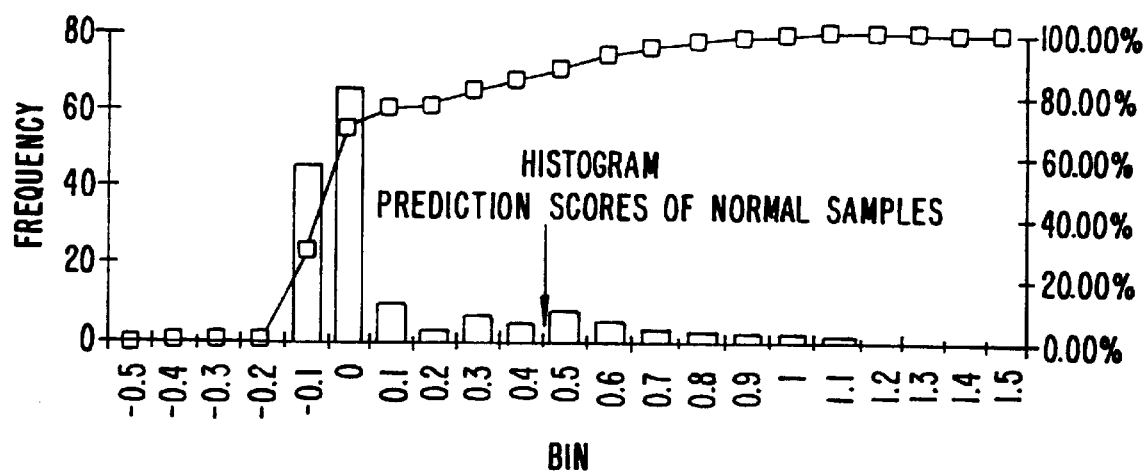
FIG. 3 is a histogram showing the prediction of scores of normal samples.
Figure 4:
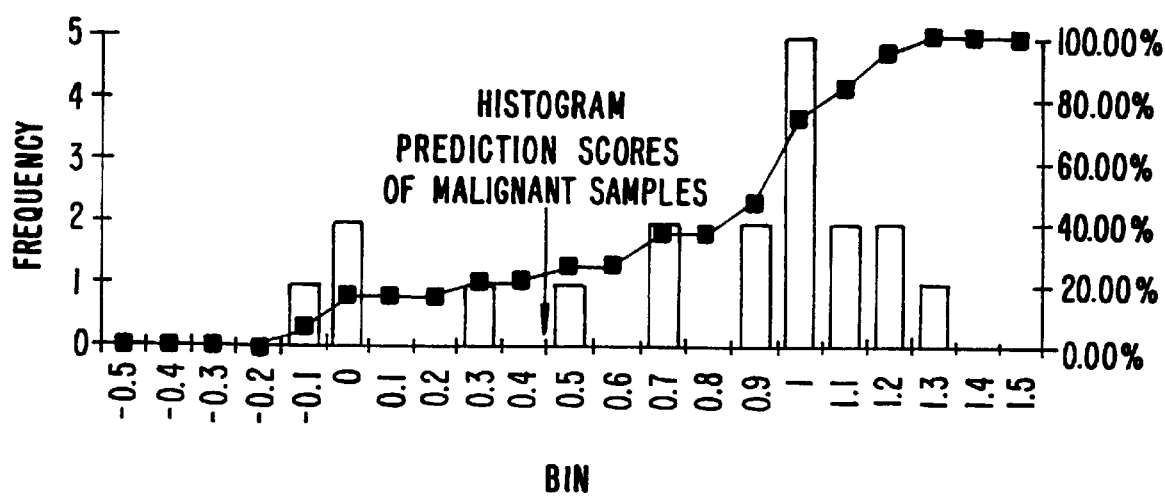
FIG. 4 is a histogram showing the prediction of scores of malignant samples.

At rank 7, the minimum prediction of the dummy variable among malignant validation samples was 0.95 (closest to 1.0), and the highest prediction of the dummy variable among normal validation samples was 0.08. Rank 7 was thereafter used to analyze the entire set of the 436 spectra. Histograms were then computed for the predicted dummy variable using 162 normal and 19 malignant samples. A break point (BP) of 0.5 provided a reasonable discrimination between the normal and malignant spectra (see FIGS. 3 and 4).

1.3 PCA Analysis of All Spectra

F-ratios were calculated for all spectra from the sample set. These values were calculated according to the methods described in Haaland, et al., *Anal. Chem.* 60:1193–1202 (1988). The F-ratios provide an indication of how similar a sample spectrum is to the calibration set. High F ratios, for examples, can result when a sample is not similar to the calibration spectra being analyzed. In this study, all spectra with F ratios $\geq 25$ were by visual inspection found to be either corrupt or significantly distinct from the calibration spectra.

A F-ratio $\geq 25$ was, thus, arbitrarily selected as the rejection threshold for exclusion of outlier spectra. This selection provides a consistency (which cannot be obtained by purely visual inspection) to the set of spectra which are then used for diagnosis. Based on this criterion, 40/436 samples were flagged out as specimens with a "poor" spectrum. The following table summarizes the diagnosis code, and the number of specimens that remained in each diagnosis class after exclusion by the F ratio criterion.

TABLE 3

| Diagnosis Code | Total Specimens | Pap smear report |
|---|---|---|
| 0 | 174 | Normal |
| a | 52 | Atypical |
| ab | 4 | Atypical with a bloody smear |
| abi | 4 | Bloody smear with atypical cells and inflammatory signs |
| ai | 27 | Atypical with evidence of inflammation |
| air | 5 | Atypical (reactive) with evidence of inflammation |
| ar | 19 | Atypical (reactive) |
| at | 2 | Atypical with atrophic pattern |
| b | 6 | Bloody smear |
| bi | 2 | Bloody smear with evidence of inflammation |
| br | 2 | Bloody smear with reactive cells |
| bx | 2 | Bloody and an acelffular smear |
| d | 8 | Dysplasia |
| i | 30 | Inflammatory |
| ib | 1 | Inflammatory and bloody smear |
| ir | 7 | Inflammatory with reactive cells |
| it | 4 | Inflammatory with atrophic pattern |
| m | 19 | Malignant or carcinoma in situ |
| r | 4 | Reactive |
| rt | 1 | Reactive with atrophic pattern |
| t | 19 | Atrophic pattern |
| tx | 3 | Acellular with atrophic pattern |
| x | 1 | Acellular |
| Total | 396 | |

Based on a 0.5 breakpoint, the 396 samples having F-ratios below 25 were classified as normal or malignant according to this linear discriminate function on the spectra. The following contingency table summarizes the results:

TABLE 4

CONTINGENCY TABLE BASED ON 0.5 BREAKPOINT

| Diagnosis | Total | Observed 0 | Observed m | Expected 0 | Expected m | $\chi^2$ | p |
|---|---|---|---|---|---|---|---|
| 0 | 174 | 148 | 26 | 132 | 42 | 2.18 | 0.140 |
| a | 52 | 39 | 13 | 39.4 | 12.6 | 2.18 | 0.140 |
| ab | 4 | 1 | 3 | 3.03 | 0.97 | 6.41 | 0.011 |
| abi | 4 | 2 | 2 | 3.03 | 0.97 | 1.46 | 0.226 |
| ai | 27 | 21 | 6 | 20.5 | 6.52 | 0.46 | 0.497 |
| air | 5 | 3 | 2 | 3.79 | 1.21 | 0.80 | 0.370 |
| ar | 19 | 16 | 3 | 14.4 | 4.59 | 0.06 | 0.810 |
| at | 2 | 0 | 2 | 1.52 | 0.48 | 5.28 | 0.022[I] |
| b | 6 | 3 | 3 | 4.55 | 1.45 | 3.00 | 0.083 |
| bi | 2 | 1 | 1 | 1.52 | 0.48 | 0.15 | 0.703 |
| br | 2 | 2 | 0 | 1.52 | 0.48 | 0.17 | 0.682 |
| bx | 2 | 1 | 1 | 1.52 | 0.48 | 0.15 | 0.703 |
| d | 8 | 4 | 4 | 6.07 | 1.93 | 4.52 | 0.034 |
| i | 30 | 21 | 9 | 22.8 | 7.24 | 3.09 | 0.079 |
| ib | 1 | 1 | 0 | 0.76 | 0.24 | 0.98 | 0.322[I] |
| ir | 7 | 6 | 1 | 5.31 | 1.69 | 0.24 | 0.622 |
| it | 4 | 3 | 1 | 3.03 | 0.97 | 0.02 | 0.880 |
| m | 19 | 4 | 15 | — | — | 38.2 | 0.000* |
| r | 4 | 2 | 2 | 3.03 | 0.97 | 1.46 | 0.226 |
| rt | 1 | 0 | 1 | 0.76 | 0.24 | 0.92 | 0.337[I] |
| t | 19 | 9 | 10 | 14.4 | 4.59 | 13.65 | 0.000* |
| tx | 3 | 2 | 1 | 2.28 | 0.72 | 0.00 | 0.945 |
| x | 1 | 1 | 0 | 0.76 | 0.24 | 0.98 | 0.322[I] |
| Totals: | 396 | 290 | 106 | | | | |
| ^Totals | 377 | 286 | 91 | | | | |

*denotes that a rounding of the number resulted in a p = 0.000.
^denotes that totals were subtracted from the samples with diagnosis malignant (code m)
[I]denotes that the method used to calculate the $\chi^2$ values necessitates the exercise of caution when interpreting the p values having a zero in one of the "observed" cells.

The above contingency table was based on the null hypothesis that with the exclusion of the malignant specimens (e.g., code m), there was no difference in the predicted distribution of each individual diagnosed category. A Chi Square test of the null hypothesis yielded a value of 44.9 at 21 degrees of freedom. The null hypothesis is rejected at the p=0.002 significance level, suggesting that at least some of the diagnoses are associated with a different frequency than being predicted as normal by spectroscopy. The computation of the Chi Square value ($\chi^2$) was performed by standard statistical methods, by excluding the malignant samples (code m) as follows: First, the sum of the numbers in column O and column m were calculated. These numbers were found to be 286 and 91, respectively. Next, for each of the "observed" values, an expected value was calculated. These expected values in column O were calculated on the basis of multiplying (the total sum of each row) by (the total sum of the observed numbers in column O divided by 377). The number 377 represents the total of all rows. For example, the "expected" value of 39.4 in column O for diagnosis atypical (code a) resulted from taking the number 52 (e.g., the total sum of the row)×(286÷377). The "expected" values in column m were calculated by the same method except for multiplying (the total sum of each row) by (the total sum of the observed numbers in column m÷377). Once again, using the atypical diagnosed samples (code a) as an example, the "expected" value of 12.6 in column m was calculated by taking the number 52 (e.g., the total sum of the row)× (91÷377). Table 5 uses the first 4 rows of the contingency table to illustrate the overall mathematical manipulations that were employed in arriving at the $\chi^2$ value.

TABLE 5

| Diagnosis | Observed (O) 0 | Observed (O) m | Expected (E) 0 | Expected (E) m | $(O-E)^2$ 0 | $(O-E)^2$ m | $(O-E)^2/E$ 0 | $(O-E)^2/E$ m |
|---|---|---|---|---|---|---|---|---|
| o | 148 | 26 | 132 | 42 | $(148-132)^2$ | $(26-42)^2$ | 1.94 | 6.09 |
| a | 39 | 13 | 39.4 | 12.6 | $(39-39.4)^2$ | $(13-12.6)^2$ | .004 | .013 |
| ab | 1 | 3 | 3.03 | 0.97 | $(1-3.03)^2$ | $(3-0.97)^2$ | 1.36 | 4.25 |

TABLE 5-continued

| | Observed (O) | | Expected (E) | | $(O-E)^2$ | | $(O-E)^2/E$ | |
|---|---|---|---|---|---|---|---|---|
| Diagnosis | 0 | m | 0 | m | 0 | m | 0 | m |
| abi | 2 | 2 | 3.03 | 0.97 | $(2-3.03)^2$ | $(2-0.97)^2$ | 0.35 | 1.09 |

$\chi^2 = \Sigma(O-E)^2/E$
= Sum of the numbers in column A + Sum of the numbers in column B for all diagnoses (with the exclusion of the malignant samples)
= 44.9 (a $\chi^2$ value of 44.9 at 21 degrees of freedom yields p = 0.002 from a $\chi^2$ distribution table)

With such a significant probability (e.g. p=0.002) for the contingency table as a whole, attempts were then made to find out which diagnosis class had a predicted distribution different than the normal samples. Accordingly, Chi Square tests (with Yates correction) were, once again, computed but this time for individual 2×2 subtables, each taken with the first row (normal diagnosis). If a, b, c, and d were to represent the numbers in the cells of the 2×2 tables as shown.

| Diagnosis | Observed | |
|---|---|---|
| | a | b |
| | c | d |

$\chi^2$ was calculated as follows:

$$\frac{[\text{absolute value of}(ad - bc) - 0.5(a + b + c + d)]^2 [a + b + c + d]}{(a + b)(c + d)(b + d)(a + c)}$$

Thus, with the malignant samples, as an example:

| | Observed | |
|---|---|---|
| Diagnosis | 0 | m |
| 0 | 148 | 26 |
| m | 4 | 15 |

$$\chi^2 = \frac{[\text{absolute value of}(148 \times 15 - 26 \times 4) - (0.5(148 + 26 + 4 + 15)])^2 [148 + 26 + 4 + 15]}{(148 + 26)(4 + 15)(26 + 15)(148 + 4)}$$

$\chi^2 = 38.2$ (based on a $\chi^2$ distribution table, a $\chi^2$ value of 38.2 corresponds to a $p < 0.001$)

A diagnosis category with a high probability value (p) indicates that samples within that category have a distribution similar to the normal specimens. While those with low probability are distributed differently. Thus, as shown in Table 4, highly significant frequencies of being predicted "malignant" were associated with samples which were diagnosed malignant, as expected (p<0.001). Also highly significant was the prediction for samples diagnosed with "atrophic pattern" (p<0.001). In addition, prediction frequencies were significantly higher than expected (p≦0.05) for specimens diagnosed as atypical with bloody smear, atypical with atrophic pattern and dysplasia (e.g., diagnosis codes ab, at, and d, respectively).

There are other ways to analyze such a contingency table (table 4) that may be advantageous for statistical accuracy. For example, the routine "PROC FREQ" in the SAS library of statistical routines (The SAS Institute Inc., Cary, N.C.) can be used to compute the probability of the null hypothesis of this entire table as well as the 2×2 contingency tables. This routine can also compute "Fisher's Exact" test, which may be preferred when some of the cells in the table are zero. Another approach that could be used to compute the probability that the distribution of the samples in one or more of the diagnosis subgroups differ from that of the sample with normal diagnosis would be to aggregate the date for all the different diagnoses (preferably excluding diagnosis of 0, d, and m, for which there is an expectation of such a difference) before constructing a 2×2 table of normal vs. all other diagnoses, which can be analyzed by the Chi Square test.

Example 2

This example provides a comparison of diagnosis with a mid-infrared technique using partial least squares analysis, and Pap smears applying conventional microscopy.

2.1 Specimen Collection

Cervical scrapings were collected by the standard brushing procedure. Exfoliated cells from each brush were harvested in separate vials which contained normal saline. The cell suspensions in each vial were dispersed with a Pasteur pipette and divided into two equal portions. One portion of the cell suspension was centrifuged and the pellet was stored frozen in liquid nitrogen until spectroscopic analysis. The other portion was spread on a microscope slide, fixed and stained by Papanicolaou stain and was examined by at least one pathologist. Out of 302 cervical scrapings that were analyzed, 206 samples were obtained from a dysplasia clinic and 96 specimens were obtained from an outpatient gynecology clinic. Three types of diagnosis were assigned to the specimens. Specimens which showed no evidence of cytological abnormality and which were obtained from individuals who had no history of cervical anomaly were classified as "normal-normal". Specimens which had normal cytology, and which were obtained from individuals who had a prior history of dysplasia were labeled as "normal-dysplasia". Specimens which exhibited evidence of dysplasia were classified according to the extent of disease using standard nomenclature. Samples which were found to have the human papilloma virus were designated with the letters "HPV", and were included in the samples diagnosed as "dysplasia".

The following table summarizes the number and the diagnosis of each type of specimen.

TABLE 6

| Specimen Type | Number |
|---|---|
| Normal-Normal | 96 |
| Normal-Dysplasia | 152 |
| Type of Dysplasia | |
| CIN I | 30 |
| CIN II | 5 |
| CIN III | 3 |
| CIN I-II | 8 |
| CIN II-III | 1 |
| CIN I-HPV | 4 |
| CIN II-HPV | 1 |
| HPV | 2 |
| Total no. of specimens | 302 |

2.2 Spectroscopic Analysis

The thawed pellets of cervical scrapings were analyzed spectroscopically, as follows: cervical scrapings were mixed with a Pasteur pipette in a syringing action, and the cell suspensions were then smeared and dried on Cleartran windows (ZnS). Mid-infrared spectra were obtained at room temperature on a Bio-Rad, Digilab FTS 165 spectrometer equipped with a DTGS detector. Spectra were collected at a resolution of 4 $cm^{-1}$ and 100 scans were co-added. A single-beam spectrum of Cleartran window was used for a background reference with each spectrum. Each spectrum was also normalized by setting the minimum absorbance at 0.0 and the maximum absorbance at 1.0. Drying of the samples resulted in specimens which were easy to manipulate and which yielded high quality spectra.

2.3 Partial Least Squares Analysis

Out of the 302 spectra that were selected for PLS analysis, 54 spectra were from specimens that had the diagnosis of dysplasia, 152 spectra were from specimens with diagnosis 'normal-dysplasia', and 96 spectra were from samples with diagnosis 'normal-normal'. A subset of the dysplastic and the 'normal-normal' spectra was then used to create a calibration set. Unless otherwise indicated, the 'normal-normal' specimens that were included in the calibration (reference) set all had spectra that appeared similar or identical to the spectrum in FIG. 1 (e.g. the spectrum reported by Wong and co-workers to characterize normal cervical scrapings). The reference specimens with dysplasia were assigned a dummy variable value of 1, and the 'normal-normal' references were assigned a value of 0. Spectra that were not included in the calibration set were used as validation samples. A break point (BP) of 0.5 was used to discriminate between the samples. All specimens with a predictive break point value<0.5 were classified as normal, and those with a predictive value≧0.5 were classified as abnormal.

2.4 Results

Three spectral regions were utilized in the analysis of the data. These regions included the zones between 1250–1000 $cm^{-1}$, 1420–1330 $cm^{-1}$, and 3000–2800 $cm^{-1}$. Rank 8 was selected as providing the best discrimination between the samples. A F-ratio≧17 was arbitrarily selected as the rejection threshold for exclusion of outlier spectra. Table 7 summarizes the results of PLS with the validation samples (e.g. 27 dysplasia, 44 "normal-normal" and 152 "normal-dysplasia" specimens).

TABLE 7

| Diagnosis | Total Number | Total Samples with F ratios < 17 | Observed N | Observed D | $\chi^2$ |
|---|---|---|---|---|---|
| Normal-Normal | 44 | 40 | 31 | 9 | |
| Normal-Dysplasia | 152 | 146 | 49 | 97 | 23 p < 0.001 |
| Dysplasia | 27 | 27 | 3 | 24 | 25.8 p < 0.001 |
| Total | 223 | 213 | | | |

N and D denote samples which were predicted as "Normal-Normal", and "Dysplasia", respectively.

As shown in Table 7, a total of 10 samples (e.g., 4 "normal-normal", and 6 "normal-dysplasia") were excluded from the study. Each of the excluded samples had a F ratio≧17. A Chi Square analysis of 2×2 subtables each taken with the first row ("normal-normal" diagnosis) based on the null hypothesis that there was no difference in the predicted distribution of specimens identified as "normal-normal", and specimens with "normal-dysplasia" or "dysplasia" yielded $\chi^2$ values of 23, and 25.83, respectively. The null hypothesis is rejected for both the "normal-dysplasia", and the "dysplasia" specimens at the p<0.001 significance level. As shown in Table 7, highly significant frequencies of predicting samples with dysplasia were associated with dysplasia samples. Also highly significantly was the difference in the distribution of specimens classified as "normal-dysplasia" relative to the "normal-normal" samples.

These results demonstrate the potential of PLS in discriminating between "normal-normal" specimens, and specimens with existing or with a prior history of dysplasia.

Example 3

This example illustrates that there are close similarities between the spectra of cervical scrapings with dysplasia, and cervical scrapings which are diagnosed as normal, but which have a prior history of dysplasia (e.g. specimens with diagnosis "normal-dysplasia").

A calibration set consisting of spectra from samples with known dysplasia, and from samples with "normal-dysplasia" using the prior data was constructed. The purpose of this analysis was to determine whether the spectra of cervical scrapings with dysplasia appeared different than the spectra of cervical scrapings with 'normal-dysplasia'. Using PCA and discriminate analysis, no significant discrimination between the two populations was observed. In the absence of observable differences, this analysis suggests that regardless of the cytological appearance of the Pap smear, in a majority of patients who have had a prior history of dysplasia the method applied to the IR spectra detects abnormal findings. Hence, IR spectroscopy, as practiced here, provides additional diagnostic information, not available by the standard cytological examination of cervical smears. Bearing in mind that the genesis of a majority of cervical dysplasias is believed to be caused by the human papilloma virus, these abnormal spectral features may directly relate to the presence of the HPV virus in the cervical scrapings of patients classified with 'normal-dysplasia'.

The IR methods of this invention can thus discriminate between a population of women having no history of dysplasia or malignancy, and one of women who are either diagnosed with dysplasia or malignancy (as detected by Pap cytology) or who have a history of dysplasia in the absence of a current diagnosis for dysplasia by Pap cytology (e.g., patients who are clinically at a high risk for dysplasia).

Example 4

This example illustrates the use of single cell infrared spectroscopy for the detection of malignant and premalignant conditions in cells.

Recent infrared spectroscopic studies of bulk cervical scrapings have revealed marked differences in the spectra of normal and malignant samples. Despite the presence of these differences, their precise origin is unknown. Although it appears intuitive that changes in the malignant cell per se give rise to the spectral abnormalities associated with cancer, no confirmation of this exists. Still further, it has been observed that in some malignant cervical samples, the cancerous cells constitute no more than 10% of the total number of epithelial cells; yet, their infrared spectra are no different from those with far greater percentages of malignant cells. Four possible explanations that may account for such an observation, include: 1) the changes in the cancer cell are so strong that they dominate the spectral contribution of the remaining $90^+\%$ of the cells, 2) the spectral changes originate from another type of cell, 3) cells not identifiable morphologically as malignant by Pap smear may have already undergone the same or similar chemical changes as the malignant cell and therefore, together with the bone fide malignant cells constitute the majority of abnormal cells, and/or 4) cancer cells secrete chemicals that absorb strongly in the mid-infrared region and it is these chemicals that contribute to the spectral changes.

To address some of these issues, the present invention provides a novel method for the acquisition of spectra from cervical scrapings on a cell by cell basis.

4.1 Materials and Methods

Cells were fixed on a custom made ZnS (Cleartran) microscope slide and examined unstained under a Bio-Rad FT-IR UMA-500 microscope linked to a FTS 165 spectrometer. The aperture was adjusted to the size of individual cells and 500 spectra were co-added at a resolution of 8 $cm^{-1}$. Spectra were analyzed in the mid-IR range (950– 3000 $cm^{-1}$). Zinc sulfide was chosen as the matrix for the support of the cells for three reasons. It provided a clear support for viewing the cells under a conventional microscope and an IR microscope. Second, the material was resistant to a number of chemicals including the stains used in Pap smears. Third, the material was well suited for the acquisition of spectra in the IR regions of interest.

(a) Preprocessing of Cervical Specimens

Cervical scrapings were collected by the standard brushing procedure. Exfoliated cells from each brush were gently shaken in vials which contained preservative solution (Preserv Cyt, CYTYC Corporation, Marlborough, Mass.). The preservative solution maintained the integrity of the exfoliated cells during transport and storage, and also served to lyse the red blood cells in the cervical scrapings. Vials containing the exfoliated cells were then treated with a CYTYC THIN PREP PROCESSOR®. The processor filtered out the mucus and non-diagnostic debris, and spread the cells in a uniform layer on the ZnS slides. In this manner, it is possible to selectively remove the majority of interfering materials from cervical scraping and obtain a uniform layer of cells while preserving the diagnostically important features of the cells. Infrared microspectroscopy was performed on unstained exfoliated cells which were recorded for their position by a cellfinder. Thereafter the slides were stained by the Papanicolaou stain, and were cytologically examined. The results of spectroscopy were then correlated with the cytological findings.

4.2 Results

Figure 5:
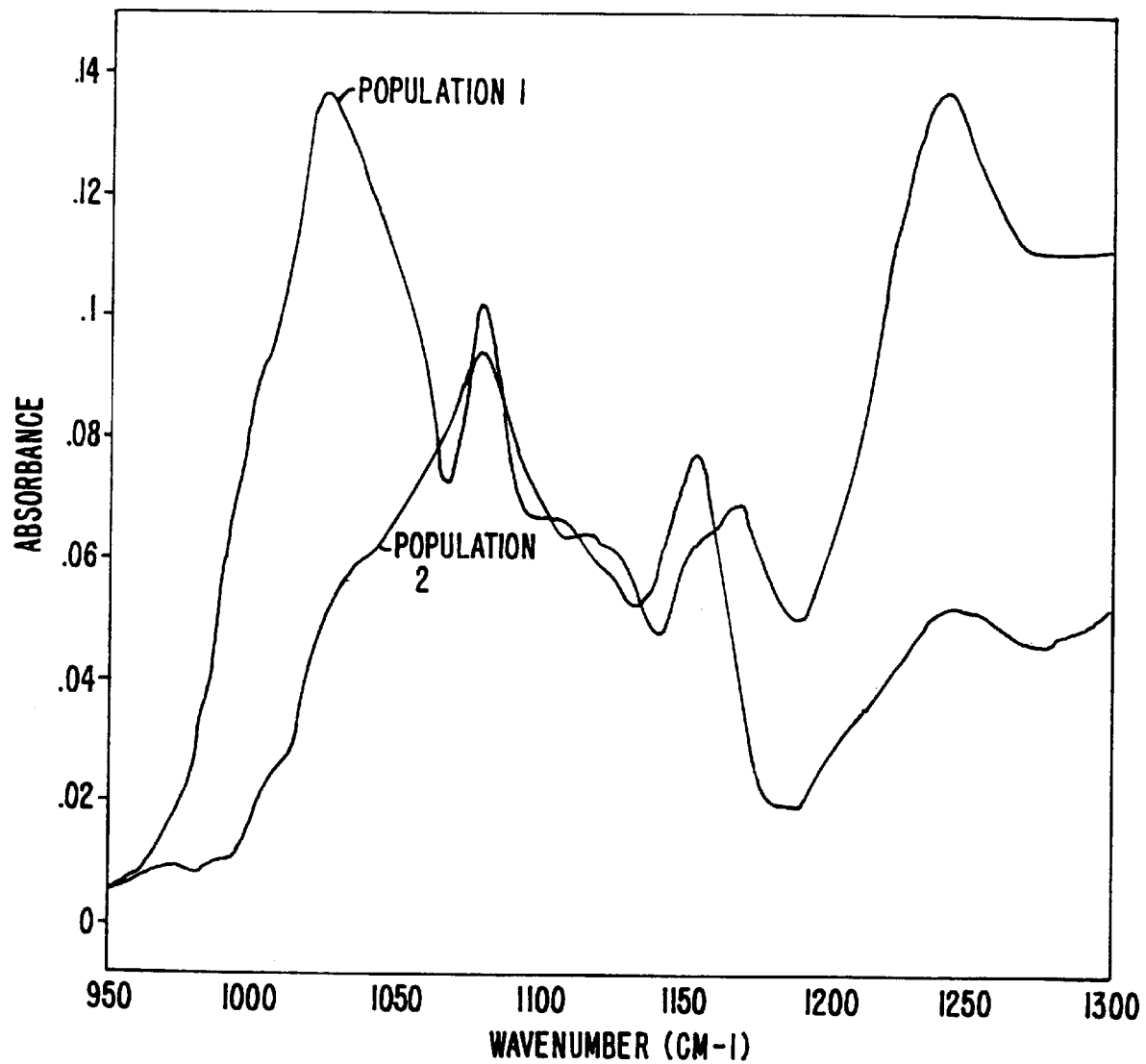
FIG. 5 shows the mid-infrared spectrum (from 950 $cm^{-1}$–1300 $cm^{-1}$) of two populations of squamous epithelial cells.
Figure 6:
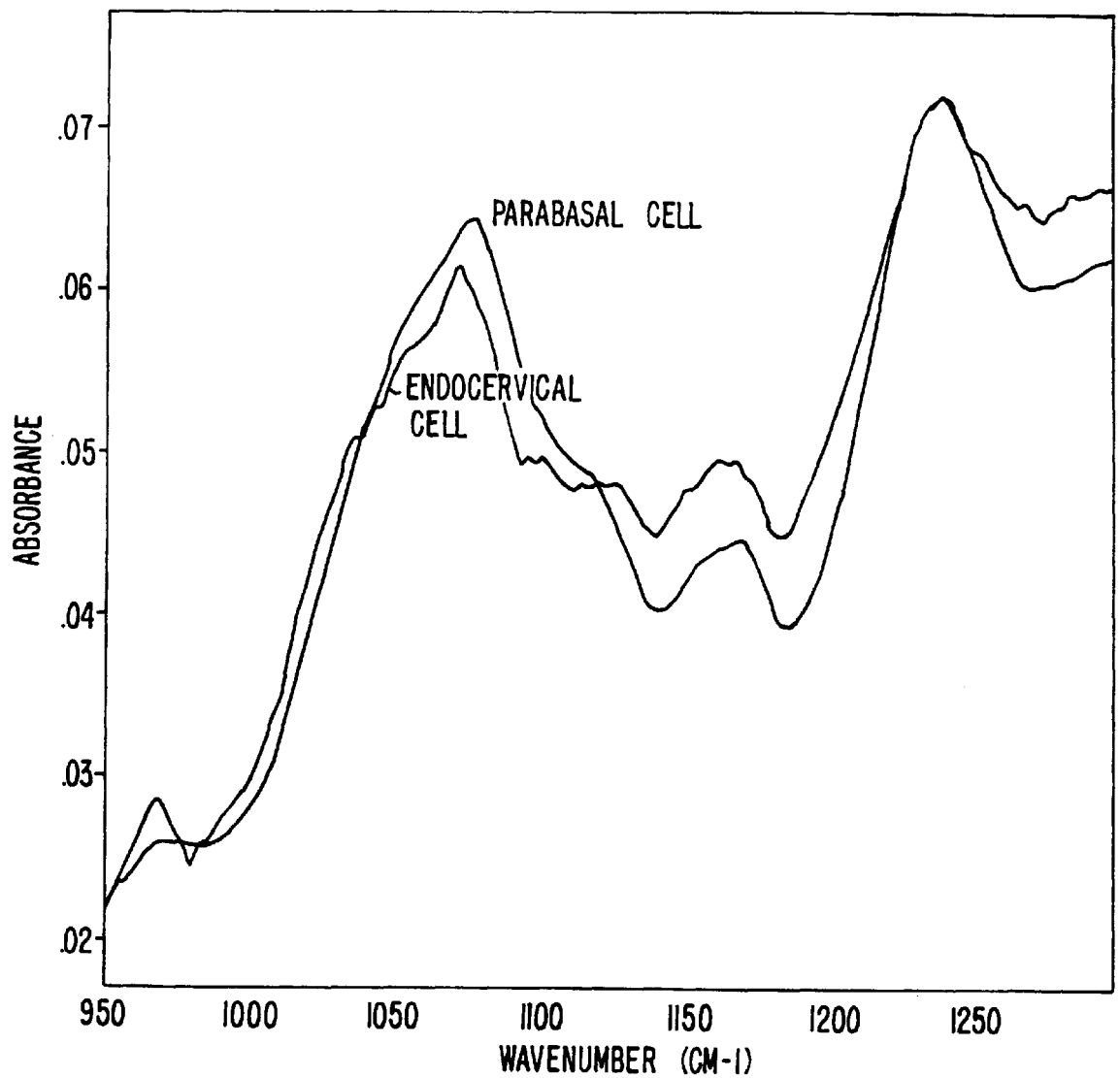
FIG. 6 shows a comparison of the mid-infrared spectra (from 950 $cm^{-1}$–1300 $cm^{-1}$) from parabasal cells and endocervical cells.

In the normal cervical scrapings four types of morphologically distinguishable cells were studied. These cells included the mature squamous epithelial cells, the intermediate squamous epithelial cells, parabasal cells and endocervical cells. Two different spectra were typically observed for the normal squamous epithelial cells. One spectrum appeared identical to the spectra for the normal cervical scrapings (FIG. 1), and the other appeared with a significantly diminished band at 1025 $cm^{-1}$. FIG. 5 shows the spectra of the two squamous cells. Squamous cells that had the typical spectrum of normal cells are referred to as Population 1, and those that lacked the 1025 $cm^{-1}$ band characteristic for glycogen are referred to as Population 2. The parabasal cells which are normally found in abundance in the cervical scrapings of menopausal patients with estrogen deficiency (e.g. a condition referred to as atrophic) exhibited spectra resembling the spectrum observed in malignant scrapings (FIG. 2, see also Wong, et al, *Proc. Natl. Acad. Sci. USA* 87:8140–8145 (1991)). This finding supported the PCA analysis in EXAMPLE 1 which found that highly significant frequencies of prediction as malignant are associated with Pap smears identified with "atrophic pattern" (e.g., contingency table 4 code t$\chi^2$=13.7 p<0.001). While the spectra of endocervical cells also exhibited a diminished peak at 1025 $cm^{-1}$, a strong band at the 1076 $cm^{-1}$ region was also observed. FIG. 6 provides a comparison of the spectra of parabasal cells and endocervical cells.

Figure 7:
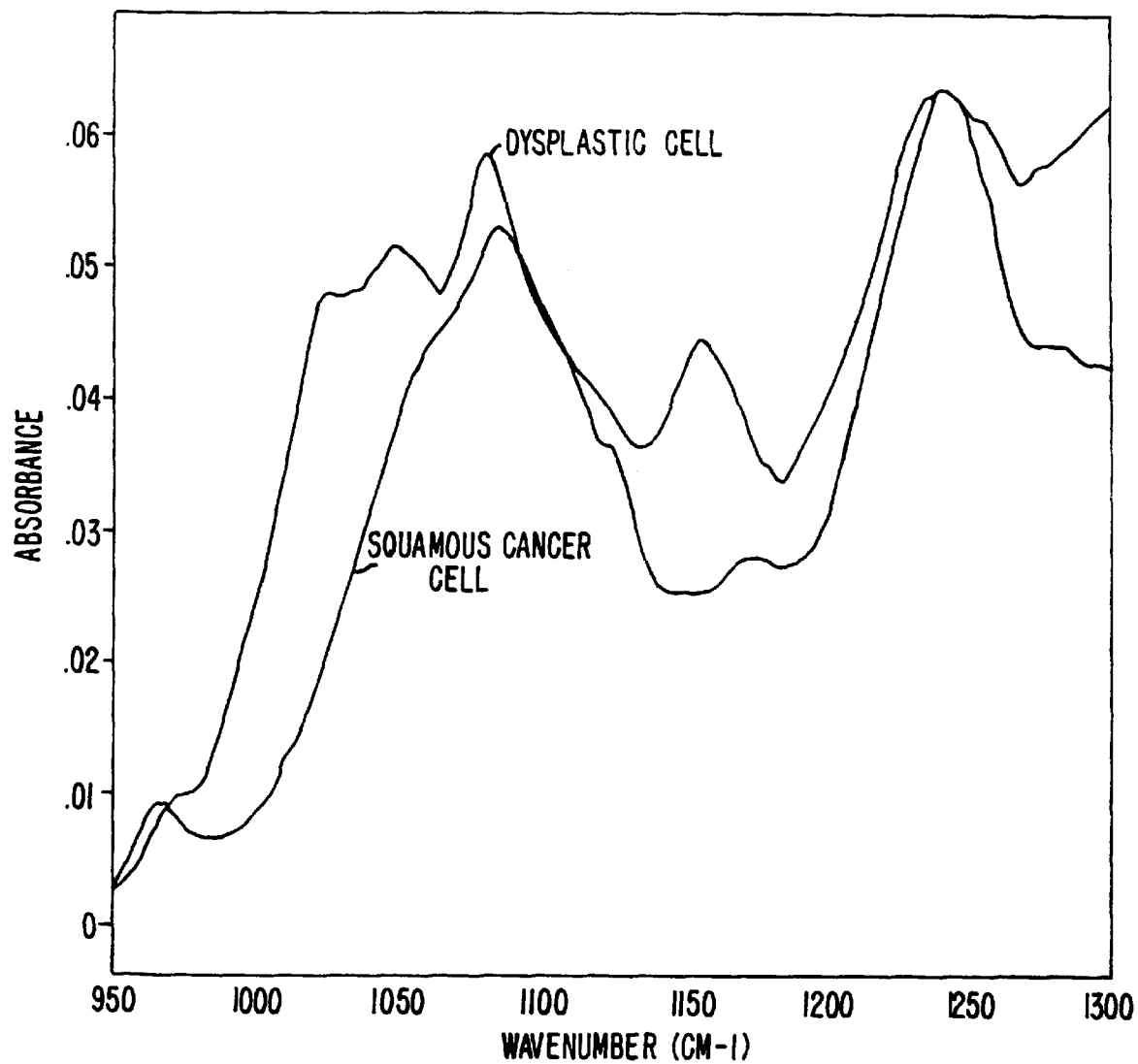
FIG. 7 shows a comparison of the mid-infrared spectra (from 950 $cm^{-1}$–1300 $cm^{-1}$) from a dysplastic cell and a squamous cancer cell.

The examination of malignant cells from patients with adenocarcinoma and squamous carcinoma of the cervix confirmed the spectral features reported by Wong, et al., ibid. All the malignant cells exhibited 1) a prominent band at 970 $cm^{-1}$; and a shift in the 1082 $cm^{-1}$ band to 1086 $cm^{-1}$. The loss in the band at 1025 $cm^{-1}$ was one of the main spectral features of the cancer cells. Microspectroscopic studies also confirmed that cells diagnosed cytologically as dysplasia (CIN III) exhibited spectra intermediate in appearance between normal and malignant. FIG. 7 exemplifies the spectral differences between a malignant cell and a dysplastic cell with CIN III characteristics.

The microscopic data clearly indicates that some cells have unique spectral features, and that differences in spectra are likely to happen if certain type of cells constitute the majority in a cervical scraping. Henceforth, in view of the fact that the Population 1 spectrum prevails as the predominant spectrum in most of the normal patients (e.g., as demonstrated by the bulk IR technique), suggests that there exists a balance between different types of cells in cervical scrapings. The mature squamous and intermediate squamous epithelial cells (e.g., Populations 1 and 2) constitute a majority in a normal cervical scraping. Thus, for the Population 1 spectrum to dominate, a balance must be maintained between these two cell types. Consequently, any method capable of detecting a shift in the number of cells corresponding to Populations 1 and 2 should also be capable of detecting the same differences in cell populations that are observed by the IR methods of this invention between women having no evidence or history of dysplasia or malignancy, and those women who are either diagnosed as having dysplasia or malignancy (as detected by Pap cytology) or who have a history of dysplasia in the absence of current diagnosis for dysplasia by Pap cytology. A shift in the balance in Populations 1 and 2, as detected by IR or another method, can thus be used to identify clinically the members of a population of women who are at high risk for dysplasia.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for the identification of a malignant or premalignant condition in an exfoliated cervical cell sample, said method comprising:

(a) drying said exfoliated cervical cell sample on an infrared transparent matrix to produce a dried cell sample;

(b) directing a beam of mid-infrared light at said dried cell sample, said beam of mid-infrared light having a frequency of from about 3000 to about 950 cm$^{-1}$ to produce absorption data for said dried cell sample; and (c) comparing said absorption data for said dried cell sample with a calibration/reference set of infrared absorption data to determine whether variation in infrared absorption occurs in said dried cell sample, at at least one range of frequencies, due to the said variation being characteristic of said malignant or premalignant condition, said comparing utilizing a partial least squares or principal component analysis statistical method and said absorption data being underivatized and unsmoothed, whereby said identification of said malignant or premalignant condition is made.

2. A method in accordance with claim 1 wherein said calibration/reference set of infrared absorption data is from a representative set of normal, dysplastic and malignant cervical cells.

3. A method in accordance with claim 2, wherein said calibration/reference set is prepared from about 100 to about 1000 reference cell samples.

4. A method in accordance with claim 2, wherein said calibration/reference set of infrared absorption data is prepared from about 100 to about 500 reference cell samples.

5. A method in accordance with claim 1, wherein said comparing utilizes principal component regression which is carried out using principal component analysis.

6. A method in accordance with claim 1, wherein said infrared transparent matrix is a matrix prepared from a member selected from the group consisting of $BaF_2$, ZnS, polyethylene film, CsI, KCl, KBr, $CaF_2$, NaCl and ZnSe.

7. A method in accordance with claim 1, wherein prior to step (a) said exfoliated cervical cell sample is dispersed, thereby separating said cervical cells from nondiagnostic debris in said sample to provide a substantially uniform suspension of cells for drying.

8. A method in accordance with claim 7, wherein said exfoliated cervical cell sample is dispersed in a preservative solution.

9. A method in accordance with claim 1, wherein said comparing utilizes principal component analysis and is confined to the frequency region of about 1200 cm$^{-1}$ to about 1000 cm$^{-1}$.

10. A method in accordance with claim 1, wherein said comparing utilizes principal component analysis and is carried out by concurrent analysis of the frequency regions of about 1250 to 1000 cm$^{-1}$, about 1420 to 1330 cm$^{-1}$ and about 3000 to 2800 cm$^{-1}$.

11. A method in accordance with claim 1, wherein said beam of mid-infrared light is directed through an aperture of individual cell size and said absorption data for said dried cell sample is produced for single cells.

12. A method in accordance with claim 1, wherein prior to step (a) said exfoliated cervical cell sample is dispersed in a preservative solution, thereby separating said cervical cells from nondiagnostic debris in said sample to provide a substantially uniform suspension of cells for drying and wherein said beam of mid-infrared light is directed through an aperture of individual cell size and said absorption data for said dried cell sample is produced for single cells.

* * * * *